United States Patent [19]
Gurmarnik

[11] Patent Number: 5,312,375
[45] Date of Patent: May 17, 1994

[54] SET FOR SPINAL ANESTHESIA

[76] Inventor: Simon Gurmarnik, 38 Garrison Rd., #1, Brooklyne, Mass. 02146

[21] Appl. No.: 82,775

[22] Filed: Jun. 28, 1993

[51] Int. Cl.$^5$ ............................................. A61M 5/00
[52] U.S. Cl. ................................. 604/264; 604/158; 604/272
[58] Field of Search ............... 604/21, 264, 272, 273, 604/158, 160

[56] References Cited

U.S. PATENT DOCUMENTS

| | | | |
|---|---|---|---|
| 2,402,245 | 6/1946 | Freeland | 604/272 |
| 2,564,977 | 8/1951 | Quang Hsi Hu | 604/272 |
| 4,083,370 | 4/1978 | Taylor | 604/272 |
| 4,524,770 | 6/1985 | Orandi | 604/160 |
| 4,721,506 | 1/1988 | Teves | 604/158 |
| 5,100,390 | 3/1992 | Lubeck et al. | 604/158 |
| 5,234,406 | 8/1993 | Drasner et al. | 604/264 |

Primary Examiner—C. Fred Rosenbaum
Assistant Examiner—N. Kent Gring
Attorney, Agent, or Firm—I. Zborovsky

[57] ABSTRACT

A set for spinal anesthesia has a spinal needle, a stylet, an introducer needle through which the spinal needle is introduced, and a clamp for fixing the spinal needle to the introducer needle to stabilize the spinal needle.

8 Claims, 2 Drawing Sheets

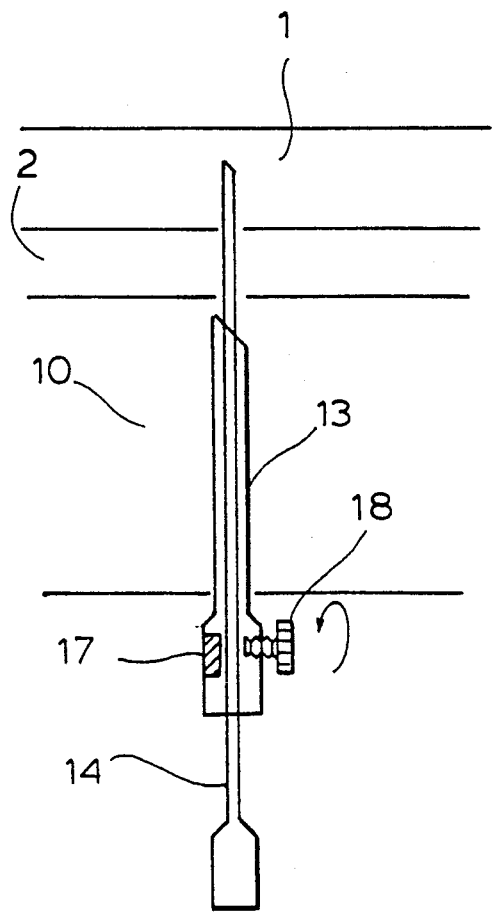
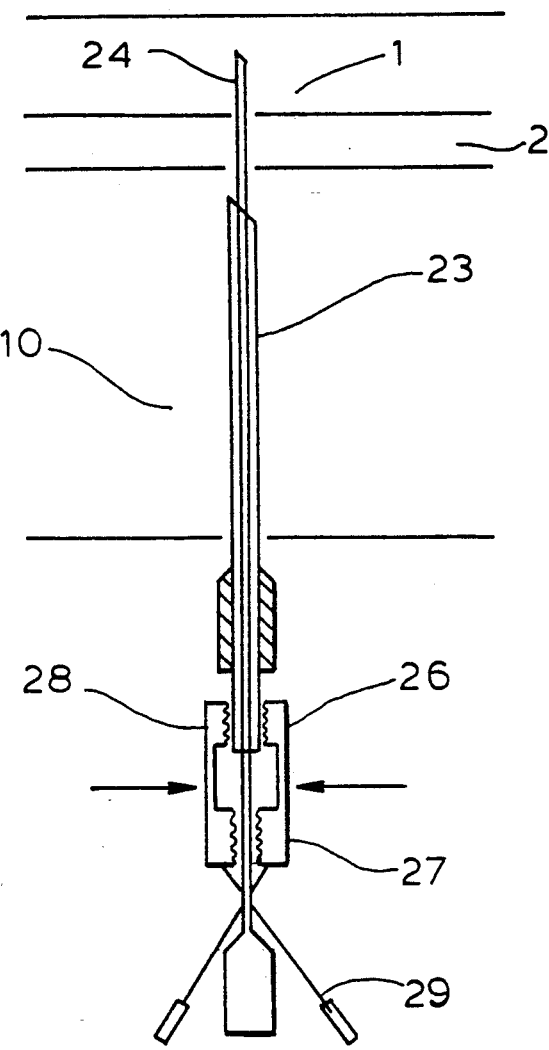
FIG. 2
FIG. 3

SET FOR SPINAL ANESTHESIA

BACKGROUND OF THE INVENTION

The present invention relates to a set for spinal anesthesia. More particularly, it relates to a set which includes an introducer needle, a spinal needle and a stylet.

Sets for spinal anesthesia of the above mentioned type are known in the art. As shown in FIG. 1, a big bore introducer needle 3 is placed within intraspinal muscles 10. Then, a small bore spinal needle 4 is placed within the introducer needle 3 to prevent its bending and curving, advanced further, and positioned within the subarachnoid space 1. The stylet 5 which extends through the spinal needle is removed and after the cerebrospinal fluid appears, a syringe with anesthetic is attached to the spinal needle and medicine is injected.

The known set possesses some disadvantages. The spinal needle positioned through the introducer needle within the subanrachnoid space is extremely unstable. It slides back and forth via the introducer needle.

SUMMARY OF THE INVENTION

Accordingly, it is an object of the present invention to provide a set for spinal anesthesia of the above mentioned type, which avoids the disadvantages of the prior art.

In keeping with these objects and with others which will be come apparent hereinafter, one feature of the present invention resides, briefly started, in a set for spinal anesthesia, in which the introducer needle and the spinal needle are fixedly connectable with one another by connecting means.

Since the spinal needle slides back and forth in the introducer needle and is therefore unstable, while the introducer needle inserted through the intraspinal muscles is stable, the spinal needle also becomes stable due to its fixed connection to the introducer needle.

The novel features of the present invention are set forth in the appended claims. The invention itself however as to its construction and its manner of operation will be best understood from the following description of preferred embodiments which is accompanied by the following drawings.

DESCRIPTION OF PREFERRED EMBODIMENTS

FIG. 2 is a view schematically showing a set for epidural anesthesia in accordance with one embodiment of the present invention; and FIG. 3 is a view schematically showing a set for spidural anesthesia in accordance with another embodiment of the present invention.

DESCRIPTION OF PREFERRED EMBODIMENTS

Figure 1:
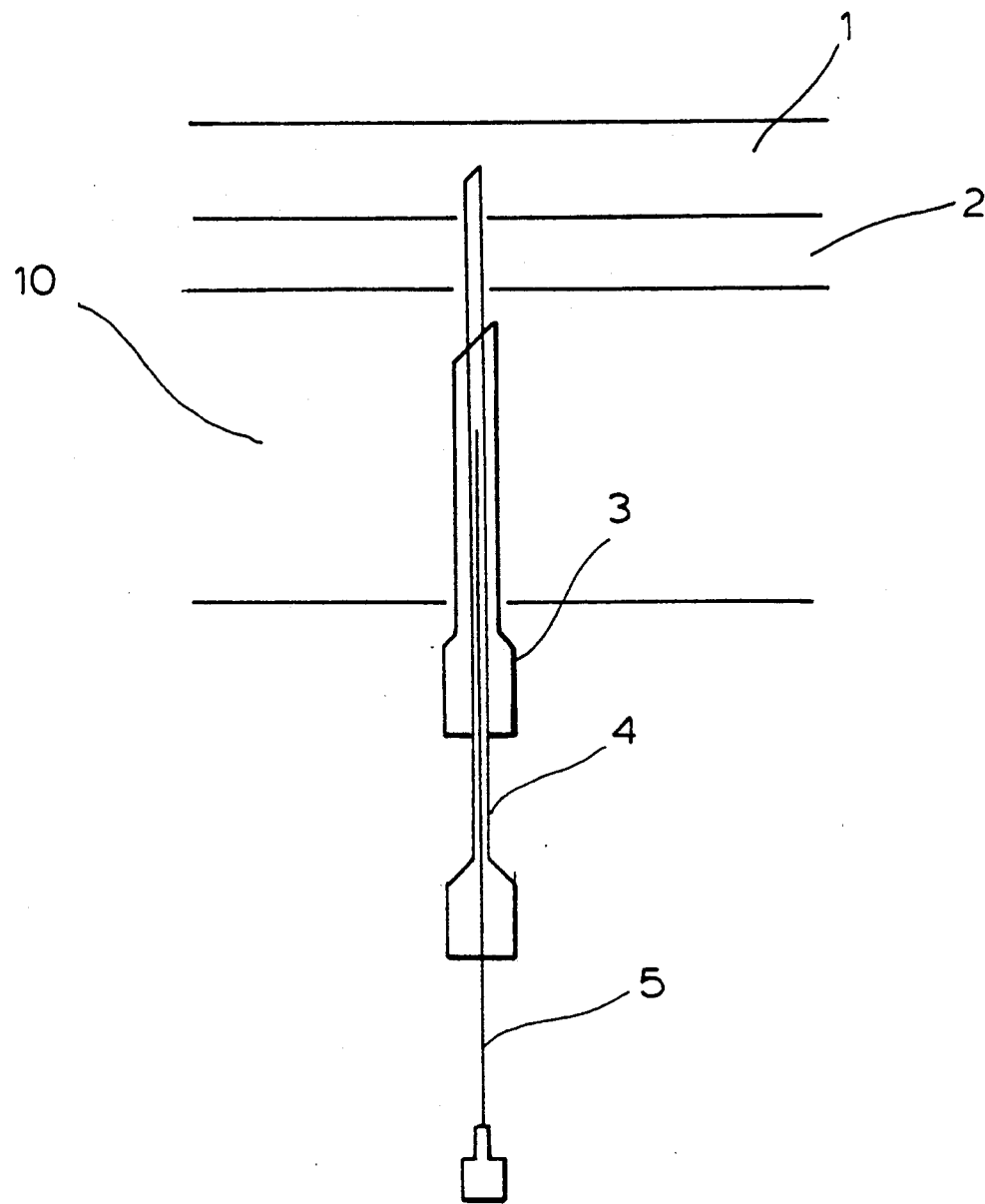
FIG. 1 is a view schematically showing a known set for epidural anesthesia in accordance with the prior art.

A set for spinal anesthesia in accordance with a first embodiment shown in FIG. 2 has a spinal needle which is identified with reference numeral 14, a stylet which conventionally extends through the inner hole of the spinal needle, and an introducer needle which is identified with reference numeral 13 and through which the spinal needle with the stylet extend. In FIGS. 2 and 3 the stylet is already removed.

The set is provided with means for immovably fixing the spinal needle and the introducer needle with one another. The fixing means in accordance with the embodiment shown in FIG. 2 includes a screw 18 which extends through a threaded lateral opening in the wall of the introducer needle 13 or its hub. Also, an elastic insert 17 is arranged inside the introducer needle 13 opposite to the threaded opening and at an opposite side of the spinal needle 14.

The set in accordance with this embodiment operates in the following manner. The introducer needle 13 is placed within the intraspinal muscle 10 is stable position. Then, the spinal needle 14 is placed within the introducer needle 13 to prevent bending and curving, is then further advanced through the epidural space 2 into the subarachnoid space 1. The stylet is removed and cerebraspinal fluid appears. After this, the screw 18 is tightened and the spinal needle becomes fixed against the rubber insert 17 with respect to the introducer needle. The spinal needle and the introducer needle thereby form a rigid, fixed structure. After this the syringe with anesthetic is attached to the spinal needle and medicine is injected.

In accordance with another embodiment shown in FIG. 3, the set also includes a spinal needle 24, a stylet and the introducer needle 23. The only difference is that the means for fixing the spinal needle and the introducer needle with one another are formed differently. Here the body of the introducer needle 24 protrudes rearwardly beyond its hub. The fixing means includes a clamp 26 which has a toothing 27 and a toothing 28 axially spaced from one another.

In order to fix the spinal needle and the introducer needle with one another, the clamp 26 is squeezed and its teeth 27 and 28 engage firmly with corresponding portions of both needles. Auxiliary projections 29 can be provided to facilitate squeezing of the clamp.

The invention is not limited to the details shown since various modifications and structural changes are possible without departing from the spirit of the invention.

What is desired to be protected by Letters Patent is set forth in the appended claims:

1. A set for spinal anesthesia, comprising
   a hollow introducer needle;
   a spinal needle introducable through said introducer needle into subarachnoid space;
   a stylet extendable through said spinal needle; and
   means for immovably fixing said spinal needle and said introducer needle with one another when said spinal needle enters the subarachnoid space, said spinal needle being freely movable inside said introducer needle between a plurality of locations, said means for immovably fixing said spinal needle and said introducer needle engaging said spinal needle and said introducer nedle transversely to their direction of elongation in any of said plurality of positions and therefore fixing said spinal needle and said introducer needle in any of said plurality of positions.

2. A set for spinal anesthesia as defined in claim 1, wherein said means for immovably fixing said spinal needle and said introducer needle includes a screw extending through a wall of said introducer needle and abutting against said spinal needle.

3. A set for spinal anesthesia as defined in claim 2, wherein said introducer needle has a hub provided with said wall and having a threaded opening, said screw being screwable through said threaded opening of said hub of said introducer needle.

4. A set for spinal anesthesia as defined in claim 2; and further comprising an elastic member located adjacent to said spinal needle at a side opposite to said screw, so that when said screw abuts against said spinal needle, said spinal needle abuts against said elastic member.

5. A set for spinal anesthesia as defined in claim 1, wherein said means for immovably fixing said spinal needle and said introducer needle includes a squeezable clamp which can be squeezed onto a portion of said introducer needle so as to fixedly connect said needles with one another.

6. A set for spinal anesthesia as defined in claim 1, wherein said means for immovably fixing a spinal needle and said introducer needle engage said spinal needle and said introducer needle in any of said plurality of positions at a same transverse location of said spinal needle and said introducer needle.

7. A set for spinal anesthesia as defined in claim 1, wherein said means for immovably fixing a spinal needle and said introducer needle engage said spinal needle and said introducer needle in any of said plurality of positions at two different locations of said spinal needle and said introducer needle which are spaced from one another in direction of elongation of said needles.

8. A set for spinal anesthesia, comprising a hollow introducer needle;

a spinal needle introducable through said introducer needle into subarachnoid space;

a stylet extendable through said spinal needle;

means for immovably fixing said spinal needle and said introducer needle with one another when said spinal needle enters the subarachnoid space, said means for immovably fixing said spinal needle and said introducer needle including a screw extending through a wall of said introducer needle and abutting against said spinal needle and an elastic member located adjacent to said spinal needle at a side opposite to said screw, so that when said screw abuts again said spinal needle, said spinal needle abuts against said elastic member, said means for immovably fixing said spinal needle and said introducer needle including a squeezable clamp which can be squeezed onto a portion of said introducer needle so as to fixedly connect said needles with one another, said clamp being tubular and has a first section provided with inner teeth and squeezable onto the portion of said introducer needle and a second section provided with inner teeth and squeezable onto the portion of the spinal needle.

* * * * *